US008669337B2

(12) United States Patent
Lu et al.

(10) Patent No.: US 8,669,337 B2
(45) Date of Patent: Mar. 11, 2014

(54) NETWORK COPOLYMER CROSSLINKED COMPOSITIONS AND METHODS OF MAKING THE SAME

(75) Inventors: Ning Lu, Chappaqua, NY (US);
Sigfredo Gonzalez, Danbury, CT (US);
Emie M. Silvestre, Yonkers, NY (US);
Geng Wang, Vienna, WV (US)

(73) Assignee: Momentive Performance Materials Inc., Waterford, NY (US)

( * ) Notice: Subject to any disclaimer, the term of this patent is extended or adjusted under 35 U.S.C. 154(b) by 657 days.

(21) Appl. No.: 12/646,333

(22) Filed: Dec. 23, 2009

(65) Prior Publication Data

US 2011/0152444 A1    Jun. 23, 2011

(51) Int. Cl.
*C08F 230/02* (2006.01)
*C08F 220/38* (2006.01)

(52) U.S. Cl.
USPC ..................... 526/274; 525/326; 526/287

(58) Field of Classification Search
USPC .................................. 525/326; 526/274, 287
See application file for complete search history.

(56) References Cited

U.S. PATENT DOCUMENTS

| | | | |
|---|---|---|---|
| 2003/0144399 A1* | 7/2003 | Matta et al. | 524/419 |
| 2007/0060729 A1* | 3/2007 | Kim et al. | 526/274 |
| 2008/0281038 A1* | 11/2008 | Takahashi et al. | 524/602 |

FOREIGN PATENT DOCUMENTS

| WO | WO 2004 099876 A1 | 11/2004 |
|---|---|---|
| WO | WO 2008 013417 A1 | 1/2008 |

OTHER PUBLICATIONS

Wu et al. (Progress in Organic Coatings 36, 1999, pp. 21-33).*

* cited by examiner

*Primary Examiner* — Kelechi Egwim
(74) *Attorney, Agent, or Firm* — Dominick G. Vicari; Joseph S. Ostroff

(57) ABSTRACT

The present invention is directed to a network composition having the reaction product of: (i) at least one anionic polymerizable ethylenically unsaturated monomer (I) selected from the group consisting of

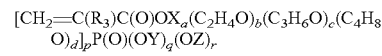

where
$R_3$=H or alkyl of 1 to about 6 carbon atoms;
X=alkyl, aryl, or alkaryl diradical connecting group of 0 to about 9 carbon atoms; a is 0 to about 100; b is 0 to about 100; c is 0 to about 100; d is 0 to about 100; q is 0 to about 2; r is 0 to about 2; p is 1 to about 3 subject to the limitation that p+q+r=3; and Y and Z is H, or metal ion; and

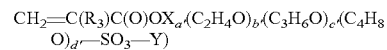

where $R_3$=H or alkyl of from 1 to about 6 carbon atoms;
X=alkyl, aryl, or alkaryl diradical connecting group of 0 to about 9 carbon atoms;
a' is 0 to about 100; b' is 0 to about 100; c' is 0 to about 100; d' is 0 to about 100; Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

27 Claims, No Drawings

NETWORK COPOLYMER CROSSLINKED COMPOSITIONS AND METHODS OF MAKING THE SAME

FIELD OF THE INVENTION

The present invention relates to network copolymer compositions, processes for their preparation, and products comprising the same.

BACKGROUND OF THE INVENTION

Network copolymer compositions can exhibit a variety of physical properties. The polymers can be modified to be hydrophilic, lipophilic and hydrophobic depending on the nature of the organic substituents. Recently, network compositions have been made by simultaneously polymerizing and cross-linking, in the presence of a free radical polymerization catalyst of a mixture of polymeizable ethylenically unsaturated monomers having particular structures that have shown utility in a variety of applications including personal care (hair conditioners, skin care and color cosmetics), textile treatments, hard surface modifiers, agricultural adjuncts, and the like. These compositions are further described and claimed below. In addition, particular methods of making these products are also shown and claimed below.

SUMMARY OF THE INVENTION

According to the invention, there is provided a network composition comprising the reaction product of:
i) at least one anionic polymerizable ethylenically unsaturated monomer (I) selected from the group consisting of

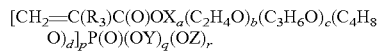

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 to about 2;
r is 0 to about 2;
p is 1 to about 3 subject to the limitation that p+q+r=3; and
Y and Z is H, or metal ion; and

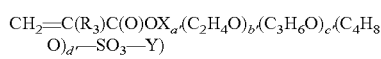

where
$R_3$=H or alkyl of from 1 to about 6 carbon atoms;
X=alkyl, aryl, or alkaryl diradical connecting group of 0 to about 9 carbon atoms;
a' is 0 to about 100;
b' is 0 to about 100;
c' is 0 to about 100;
d' is 0 to about 100;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

Another aspect of the present invention is directed to a method of producing the network compositions of the present invention by polymerizing the monomers set forth above under free radical polymerization conditions in various solvents and under temperatures used to polymerize acrylates.

Additional embodiments are also part of the present invention, which are further described in the Detailed Description of the Invention below.

DETAILED DESCRIPTION OF THE INVENTION

According to the present invention, a network composition comprising the reaction product of:
i) at least one anionic polymerizable ethylenically unsaturated monomer (I) selected from the group consisting of

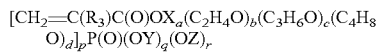

where
$R_3$=H or alkyl of 1 to about 6 carbon atoms;
X=alkyl, aryl, or alkaryl diradical connecting group of 0 to about 9 carbon atoms; a is 0 to about 100, 1 to about 100, preferably O to about 40 and more preferably about 0 to about 15;
b is 0 to about 100, 1 to about 100, preferably O to about 40 and more preferably about 0 to about 15;
c is 0 to about 100, 1 to about 100, preferably O to about 40 and more preferably about 0 to about 15;
d is 0 to about 100, 1 to about 100, preferably O to about 40 and more preferably about 0 to about 15;
q is 0 to about 2;
r is 0 to about 2;
p is 1 to about 3 subject to the limitation that p+q+r=3; and
Y and Z is H, or metal ion; and

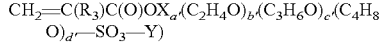

where
$R_3$=H or alkyl of from 1 to about 6 carbon atoms;
X=alkyl, aryl, or alkaryl diradical connecting group of 0 to about 9 carbon atoms;
a' is 0 to about 100, 1 to about 100, preferably O to about 40 and more preferably about 0 to about 15;
b' is 0 to about 100, 1 to about 100, preferably O to about 40 and more preferably about 0 to about 15;
c' is 0 to about 100, 1 to about 100, preferably O to about 40 and more preferably about 0 to about 15;
d' is 0 to about 100, 1 to about 100, preferably O to about 40 and more preferably about 0 to about 15;
Y is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

One embodiment of the present invention includes up to about 0.5 to about 50 percent by weight of the total weight of monomers, of one or more additional monomer, preferable any acrylic acid/acrylate, methacrylic acid/methacrylate, or monomers such as acrylamides, vinyl acetate and styrene, which are copolymerizable with (i). Any organic acrylate or methacrylate can be employed as the comonomers in the composition. Examples of such monomers include, but are not limited to, acrylic acid and methacrylic acid or the derivatives such as methyl, ethyl, butyl, amyl, 2-ethylhexyl, cyclohexyl, vinyl, ally, hydroxyethyl, perfluoroethyl, isobornyl, phenoxyethyl, tetraethylene glycol, tripropylene glycol, trimethylolpropane, polyoxyalkylene.

According to still another aspect of the present invention further provides a network composition described above wherein the cross-linking agent is a polyfunctional vinylidene monomer containing at least two unsaturated groups. Examples of polyfunctional vinylidene monomers of the network composition is selected from the group consisting of butadiene, isoprene, divinyl benzene, allyl acrylates, polyalkylene glycol diacrylates and dimethacrylates. Other crosslinking agents include diallyl esters and dimethallyl esters and other crosslinking agents listed and described in U.S. Pat. No. 4,509,949 herein incorporated in its entirety by reference.

In still yet another aspect of the present invention, a network composition as described above is provided wherein the composition comprises about 40 to about 99, preferably 50 to about 85, more preferably about 60 to about 75 weight percent based on the total weight of the monomers of at least one anionic polymerizable ethylenically unsaturated monomer (I), about 0.5 to about 50, preferably about 5 to about 40, more preferably about 10 to about 30 weight percent based on the total weight of the monomers of the additional monomers and about 0.1 to about 10, preferably about 2 to about 8, more preferably about 3 to about 6 weight percent based on the total weight of the monomers of said cross-linking agent.

Both the acrylate cross-links and the polyether substituents are capable of hydrogen bonding with water and other hydroxylic solvents, increasing content of either, all other composition variables remaining constant, will tend to increase the water swellability of the resulting cross-linked network polymer. Because it is possible to vary the compositional parameters of the cross-linked network copolymers of the invention in an almost limitless fashion, some compositions are both water swellable and oil swellable while others are only water swellable or oil swellable, and some compositions will not be swellable with any of the solvents discussed herein. The amount of crosslinking present in the crosslinked network may be characterized with respect to the degree of swelling exhibited by the network in the fluid.

The cross-linked structure of the network of the present invention is effective to allow the network to be swollen from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the silicone composition of the present invention to leave the original volume, that is, the volume of the copolymer network in the absence of the fluid.

In one aspect of the present invention the network composition of the present invention can be swollen by a solvent such as water.

According to yet another aspect of the present invention a network composition comprising a reaction product of monomer (I) provided below and has a subscript p equal to 2 or 3, no additional cross linking agent is necessary. That is, a network composition comprising at least one anionic polymerizable ethylenically unsaturated monomer (I)

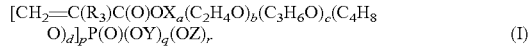
(I)

where
  $R_3$=H or alkyl of 1 to about 6 carbon atoms;
  X=alkyl, aryl, or alkaryl diradical connecting group of 0 to about 9 carbon atoms; a is 0 to about 100;
    b is 0 to about 100;
    c is 0 to about 100;
    d is 0 to about 100;
    q is 0 to about 2;
    r is 2 or 3;

p is 1 to about 3 subject to the limitation that p+q+r=3; and Y and Z is H, or metal ion; and (ii) one or more additional monomers (II) selected from the group consisting of acrylic acid/acrylate, methacrylic acid/methacrylate, acrylamides, vinyl acetate and styrene, which are copolymerizable with (I). No additional crosslinking agent is necessary for the reaction of monomer (I) and monomer (II) in this embodiment of the present invention since monomer (I) having a p value of 2 or 3 is essentially a polyunsaturated molecule having 2 or 3 double bonds and therefore acts as a cross-linking agent.

In one embodiment of the present invention, the network composition is a solid or solid gel material, typically having a creamy consistency, wherein the copolymer network acts as a means for gelling the fluid to reversibly impart characteristics of a solid to the fluid. At rest, the network polymer composition exhibits the properties of a solid gel material. The network polymer composition of the present invention exhibits high stability and resistance to syneresis, that is, the composition exhibits little or no tendency for fluid to flow from the composition and imparts high stability and syneresis resistance to personal care compositions, which include the silicone composition as a component. The high stability and syneresis resistance persists with prolonged aging of such silicone compositions and personal care compositions. However, fluid may be released from the network by subjecting the network polymer composition to a shearing force, such as, for example, by rubbing the composition between one's fingers, to provide improved sensory feel characteristic of the fluid component of the silicone material.

Water (or a water equivalent such as a non-aqueous hydroxylic solvent), siloxane, linear or cyclic, or lipophillic fluid (oil swelling agent, oil swellable) may be used as the swelling agent. Lipophilic fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In another embodiment of the invention, the copolymer network is a crosslinked network that is insoluble in various fluid components, but that is capable of being swollen by the fluid. The amount of crosslinking present in the crosslinked network may be characterized with respect to the degree of swelling exhibited by the network in the fluid. In another preferred embodiment, the crosslinked structure of the network is effective to allow the network to be swollen by water, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the network polymer composition of the present invention to leave the original volume, that is, the volume of the copolymer network in the absence of the fluid. In another preferred embodiment, the crosslinked structure of the network is effective to allow the network to be swollen by a lipophilic fluid, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the network polymer composition of the present invention to leave the original volume, that is, the volume of the polyacrylate siloxane copolymer network in the absence of the fluid.

In another preferred embodiment, the crosslinked structure of the network is effective to allow the network to be swollen by a low molecular weight silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the network composition of the present invention to leave the original volume, that is, the volume of the copolymer network in the absence of the fluid.

In yet another embodiment of the present invention, the fluid component of the present invention comprises an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

According to yet another aspect of the present invention a network composition comprising the reaction product of at least one anionic polymerizable ethylenically unsaturated monomer (I) selected from the group consisting of $CH_2=C(CH_3)C(O)O(C_3H_6O)_6P(O)(OH)(ONa)$, $CH_2=C(CH_3)C(O)O(C_3H_6O)_6P(O)(OH)_2$, $CH_2=CHC(O)O(C_3H_6O)_6P(O)(OH)(OH)_2$, and $CH_2=C(CH_3)C(O)O(C_2H_4O)_nP(O)(OH)_2$ and combinations thereof; additional monomers (II) selected from the group consisting of: $CH_2=CHC(O)OH$ and $CH_2=C(CH_3)C(O)O(C_3H_6O)_6H$ and combinations thereof; and cross-linking agent (III) selected from the group consisting of $CH_2=CHC(O)O(C_2H_4O)_nC(O)OCH=CH_2)$, $CH_2=C(CH_3)CO_2CH_2]_3CC_2H_5$, $[CH_2=C(CH_3)C(O)O(C_3H_6O)_6]_2P(O)(OH)$ and combinations thereof.

Another aspect of the present invention is directed to a method for producing network polymer compositions of the present invention. Using the monomers described above, the monomers are polymerized under free radical polymerization conditions. The polymerizations are conducted in various solvents using catalysts and temperatures known in the art for polymerizing acrylates.

Examples of solvents that can be used in the present method include but are not limited to silicone fluid, water, alcohol, ester, hydrocarbon fluid or organic oil. Examples of catalyst that can be used in the method of the present invention include but are not limited to free radical catalysts such as peroxides such as hydrogen peroxide, ammonium persulfate, potassium persulfate and the like. Organic peroxy catalysts, such as dialkyl peroxides, e.g., diisopropyl peroxide, dilauryl peroxide, di-t-butyl peroxide, dicumyl peroxide, alkyl hydrogen peroxides such as t-butyl hydrogen peroxide, t-amyl hydrogen peroxide, cumyl hydrogen peroxide, diacyl peroxide, for instance acetyl peroxide, lauroyl peroxide, benzoyl peroxide, peroxy ester such as ethyl peroxybenzoate, pavalate peroxide, the azo compounds such as 2-azobis(isobutyronitrile), 1-azobis(1-cyclohexanecarbonitrile) and the like and other free radical generating catalysts.

The network polymer composition may be further processed under low or high shear to adjust the viscosity and sensory feel of the composition. This may be achieved, for example, by subjecting the composition to a moderate to high shearing force. Optionally, one or more fluids may be added to the silicone composition prior to the shearing. The network polymer composition of the present invention may be in a gel form, which contains the polymer itself and the solvents. It can also be processed (i.e. evaporated) to remove part or all of the solvents.

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges. As used herein, integer values of stoichiometric subscripts refer to molecular species and non-integer values of stoichiometric subscripts refer to a mixture of molecular species on a molecular weight average basis, a number average basis or a mole fraction basis. In the case of mixtures of the compounds of the present invention, it should be readily apparent that the stoichiometric subscripts of mixtures would have average values for the subscripts that may be either integral or non-integral in contrast to those of pure compounds.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "cross-linked polymers" means polymer molecules which are built from monomers which are linked together at many points other than their ends and as a result molecules with large size form and the material is non-pourable solid or gel-like which cannot be dissolved in any solvent. Cross-links are bonds that link one polymer chain to another. They can be covalent bonds or ionic bonds. "Polymer chains" can refer to synthetic polymers or natural polymers. In synthetic polymers, crosslinking refers to the use of cross-links to promote a difference in the polymers' physical properties.

The copolymers in our invention are "non-crosslinked", which means that their monomers are either not linked together at points other than their ends or the linkages between the polymers are so few that the copolymer is either liquid or can be dissolved in at least one solvent.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the present invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Other optional ingredients may be added in the compositions of the present invention including coupling agents, e.g., silane coupling agents, curing aids, e.g., including activators, retarders and accelerators, processing additives such as oils, plasticizers, tackifying resins, silicas, other fillers, pigments, fatty acids, zinc oxide, waxes, antioxidants and anti-ozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

The compositions of the present invention can be used commercially as a demulsifying agents, in agricultural compositions including fertilizers, in cosmetics and personal care products, in household cleaners, in coating compositions such as waxes and the like, in water processing apparatuses as well as other products.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

SYNTHETIC EXAMPLES

Example 1

Preparation Network Polymer Composition 1

Mixture through 1 through 4 in Table I were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25 C after two hours. Mixture 4 was then added and the mixture was mixed for 30 minutes to give an off-white soft solid.

TABLE I

| INGREDIENTS | WEIGHT (grams) |
| --- | --- |
| Mixture 1 | |
| Trimethylolpropane trimethacrylate | 0.2 |
| Acrylic acid | 3.9 |
| Phosphate mono-ester of polypropylene glycol mono-methacrylate (MW = 500) | 151.2 |
| Phosphate di-ester of polypropylene glycol mono-methacrylate (MW = 900) | 15.4 |
| Polyproplyeneglycol mono-methacrylate (MW = 400) | 8.4 |
| Tergital TMN-6 | 7.0 |
| Wa | 443.8 |
| Sodium hydroxide solution (40 wt % in water) | 39.7 |
| Mixture 2 | |
| Sodium bisulfite solution (10% in water) | 1.8 |
| Ferrous ammonium sulfate solution (0.2% in water) | 3.5 |
| Mixture 3 | |
| Potassium persulfate solution (4.5 wt % in water) | 21.0 |
| Mixture 4 | |
| Sodium metabisulfite solution (10 wt % in water) | 35.0 |

*Tergital TMN-6 is a Branched Secondary Alcohol Ethoxylates, available at Dow Chemicals.

Example 2

Preparation of Network Polymer Composition II

Mixture 1 through 4 in Table II were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25° C. after two hours. Mixture 4 was then added and the mixture was mixed for 30 minutes to give an off-white soft solid.

TABLE II

| INGREDIENTS | WEIGHT (grams) |
| --- | --- |
| Mixture 1 | |
| Phosphate mono-ester of polypropylene glycol mono-methacrylate (MW = 500) | 108.0 |
| Phosphate di-ester of polypropylene glycol mono-methacrylate (MW = 900) | 11.0 |
| Polyproplyeneglycol mono-methacrylate (MW = 400) | 6.0 |
| Tergital TMN-6* | 5.0 |
| Sag 330** | 0.3 |
| Water | 314.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals.
**Sag 330 is a silicone-based antifoam emulsion, available at Momentive Performance Materials.

Example 3

Preparation of Network Polymer Composition III

Part 1 through 3 in Table III were used to prepare Network Polymer Composition III. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE III

| INGREDIENTS | WEIGHT (grams) |
| --- | --- |
| Part 1 | |
| Phosphate mono-ester of polypropylene glycol mono-methacrylate (MW = 500) | 25.9 |
| Phosphate di-ester of polypropylene glycol mono-methacrylate (MW = 900) | 2.6 |
| Polyproplyeneglycol mono-methacrylate (MW = 400) | 1.4 |
| Water | 70.0 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 4

Preparation of Network Polymer Composition IV

Part 1 through 3 in Table IV were used to prepare Network Polymer Composition IV. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE IV

| INGREDIENTS | WEIGHT (grams) |
| --- | --- |
| Part 1 | |
| Polyethyleneglycol diacrylate | 0.08 |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 5

Preparation of Network Polymer Composition V

Part 1 through 3 in Table V were used to prepare Network Polymer Composition V. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE V

| INGREDIENTS | WEIGHT (grams) |
| --- | --- |
| Part 1 | |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |
| Part 2 | |
| Sodium bisulfite solution | 0.15 |
| Part 3 | |
| Potassium persulfate | 0.3 |

Example 6

Use of Network Polymer Composition I as an Aqueous Phase Thickener

The thickened aqueous compositions of Example 6 were made by combining the listed ingredients in the relative amounts set forth in Table VI, according to the following procedures. Network Polymer Composition I prepared according to Example 1 was missed with D.I. water using an overhead mixer at 700 RPM for 10 minutes. The viscosities of the resulting materials (measured after 24 hours) are listed in Table VI.

TABLE VI

| | Sample 6-1 | Sample 6-2 | Sample 6-3 | Sample 6-4 |
| --- | --- | --- | --- | --- |
| Ingredients | | | | |
| Network polymer composition I (grams) | 8.3 | 10 | 11.7 | 13.3 |
| Water (grams) | 41.7 | 40 | 38.3 | 36.7 |
| Property | | | | |
| Viscosity (cPs) | 4000 | 15000 | 128000 | 216500 |

Example 7

Use of Network Polymer Composition II as an Aqueous Phase Thickener

The thickened aqueous compositions of Example 7 were made by combining the listed ingredients in the relative amounts set forth in Table VII, according to the following procedures. Network Polymer Composition II prepared according to Example 2 was missed with D.I. water using an overhead mixer at 700 RPM for 10 minutes. The viscosities of the resulting materials (measured after 24 hours) are listed in Table VII.

| | Sample 7-1 | Sample 7-2 | Sample 7-3 | Sample 7-4 |
| --- | --- | --- | --- | --- |
| Ingredients | | | | |
| Network polymer composition II (grams) | 7.1 | 8.3 | 10 | 12.5 |
| Water (grams) | 42.9 | 41.7 | 40 | 37.5 |
| Property | | | | |
| Viscosity (cPs) | 22000 | 40500 | 71000 | 105500 |

Example 8

Use of Network Polymer Composition III. IV and V as Aqueous Phase Thickeners

The thickened aqueous compositions of Example 8 were made by combining the listed ingredients in the relative amounts set forth in Table VIII, according to the following procedures. Network Polymer Composition III, IV and V were prepared according to Example 3, 4 and 5 respectively. The ingredients were mixed using an overhead mixer at 700 RPM for 10 minutes. The viscosities of the resulting materials (measured after 24 hours) are listed in Table VIII.

TABLE VIII

|  | Sample 8-1 | Sample 8-2 | Sample 8-3 |
|---|---|---|---|
| Ingredients |  |  |  |
| Network polymer composition III (grams) | 16.7 |  |  |
| Network polymer composition IV (grams) |  | 16.7 |  |
| Network polymer composition V (grams) |  |  | 16.7 |
| Water (grams) | 83.3 | 83.3 | 83.3 |
| Property |  |  |  |
| Viscosity (cPs) | 69000 | 75500 | 65000 |

Example 9

Use of Network Polymer Composition II as an Aqueous Phase Thickener

The thickened aqueous compositions of Example 9 were made by combining the listed ingredients in the relative amounts set forth in Table IX, according to the following procedures. Network Polymer Composition II prepared according to Example 2 was missed with D.I. water using an overhead mixer at 700 RPM for 10 minutes. The viscosities of the resulting materials (measured after 24 hours) are listed in Table IX.

TABLE IX

|  | Sample 10 |
|---|---|
| Ingredients |  |
| Network polymer composition II (grams) | 20 |
| Water (grams) | 80 |
| Property |  |
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 10

Use of Network Polymer Composition II as an Aqueous Phase Thickener

The thickened aqueous compositions of Example 10 were made by combining the listed ingredients in the relative amounts set forth in Table X, according to the following procedures. Network Polymer Composition I prepared according to Example 2 was missed with D.I. water using an overhead mixer at 700 RPM for 10 minutes. pH was adjusted by using glycolic acid. The viscosities of the resulting materials (measured after 24 hours) are listed in Table X. Network Polymer Composition II provided effective thickening of the aqueous solution in the range of pH 4-9.

TABLE X

|  | Sample 10 |
|---|---|
| Ingredients |  |
| Network polymer composition II (grams) | 20 |
| Water (grams) | 80 |
| Property |  |
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 11

Use of Network Polymer Compositions I-V in Moisturizer Compositions

The moisturizing formulations of Example 11 were made by combining the listed ingredients in the relative amounts set forth in Table XI, according to the following procedures. Network Polymer Composition I-V were prepared according to Example 1-5 respectively. The ingredients were mixed using an overhead mixer at 700 RPM for 10 minutes. Panel tests showed that Sample 11-2 to 11-5, when applied on skin, provided significantly lower tack, lighter and more cushioning feel than Comparative Sample 11.

TABLE XI

| Ingredients | Sample 11-1 | Sample 11-2 | Sample 11-3 | Sample 11-4 | Sample 11-5 | Comparative Sample 11 |
|---|---|---|---|---|---|---|
| Network polymer composition I (grams) | 15 |  |  |  |  |  |
| Network polymer composition II (grams) |  | 15 |  |  |  |  |
| Network polymer composition III (grams) |  |  | 15 |  |  |  |
| Network polymer composition IV (grams) |  |  |  | 15 |  |  |
| Network polymer composition V (grams) |  |  |  |  | 15 |  |
| *Hispagel 200 |  |  |  |  |  | 15 |
| Glycerin | 20 | 20 | 20 | 20 | 20 | 20 |
| Water (grams) | 65 | 65 | 65 | 65 | 65 | 65 |

*Hispagel 200 is a glycerin/glyceryl polyacrylate, available at Cognis.

Example 12

Use of Network Polymer Compositions I in a Sunscreen Lotion Composition

The sunscreen lotion compositions in Example 12 were made by combining the ingredients listed in Table XII, according to the following procedure: (1) Part A was made by mixing all the ingredients using an overhead mixer at 700 RPM until uniform; (2) Part B was mixed in a separate container and then added to Part A; (3) the mixture was then mixed until uniform. Stable o/w emulsions were prepared.

Sample 12 provided a lighter and silkier feel than Comparative Sample 12. It also exhibited lower tack.

TABLE XII

| Ingredients | Sample 12 Weight (grams) | Comparative Sample 12 Weight (grams) |
|---|---|---|
| Part A | | |
| Network polymer composition I | 8 | |
| Pemulen TR-2* | | 0.2 |
| Water | 26 | 33.8 |
| Glycerin | 2 | 2 |
| Part B | | |
| Octyl methoxycinnamate | 3 | 3 |
| Octyl salicylate | 1 | 1 |

*Pemulen TR-2 is an Acrylates/C10-30 Alkyl Acrylate Crosspolymer, available at Lubrizol.

Example 13

Use of Network Polymer Compositions I in a Color Cosmetic Composition

The color cosmetic compositions in Example 13 were made by combining the ingredients listed in Table XIII and mixing using an overhead mixer until uniform. Panel test showed that Sample 13, when applied on skin, exhibited better spreading and sensory than Comparative Example 13.

TABLE XIII

| Ingredients Part A | Sample 13 Weight (grams) | Comparative Sample 13 Weight (grams) |
|---|---|---|
| Network polymer composition I | 20 | |
| Hispagel 200* | | 20 |
| Water | 77 | 77 |
| Aeroxide TiO$_2$ P25** | 3 | 3 |

*Hispagel 200 is a glycerin/glyceryl polyacrylate, available at Cognis.
**Aeroxide TiO$_2$ P25 is a titanium dioxide, available at Evonik Degussa.

Example 14

Use of Network Polymer Compositions I in a Rinse-Off Hair Conditioner Composition The rinse-off hair conditioner compositions of Sample 14 and Comparative Example 14 were made by combining the ingredients listed in Table XIV, according to the following procedure: (1) Part A was made by combining the ingredients and mixing at 60° C. until uniform; (2) Part B was mixed in a separate container and then added to Part A; (3) the mixture was then mixed until uniform. Panel tests showed that Network Polymer Composition I improved the softness and sleekness of the hair.

TABLE XIV

| Ingredients | Sample 14 Weight (grams) | Comparative Sample 14 Weight (grams) |
|---|---|---|
| Part A | | |
| Network polymer composition I | 25.5 | 0 |
| SF1632** | 5 | 5 |
| D.I. water | 59.5 | 85 |
| Tergital TMN-6* | 0.1 | 0.1 |
| Part B | | |
| D.I. water | 9.8 | 9.8 |
| Polyquaternium-10 (Ucare polymer JR30M) | 1 | 1 |

*Tergital TMN-6 is a Branched Secondary Alcohol Ethoxylates, available at Dow Chemicals;
**SF1632-C16-18 alkyl dimethicone, available at GE silicones; and Polyquaternium-10 UCARE polymer JR30M, available at Dow Chemicals.

Example 15

Preparation of Network Polymer Composition XV

Mixture 1 through 4 in Table XV were used to prepare Network Polymer Composition I. Mixture 1 was placed in a 2 L mixer. Nitrogen was bubbled through for 30 minutes to remove oxygen from the system. The mixture was heated to 55° C. under nitrogen and held at the temperature. Mixture 2 and mixture 3 were added over a 5 minute time period. The mixture was cooled to 25° C. after two hours. Mixture 4 was then added and the mixture was mixed for 30 minutes to give an off-white soft solid. The soft solids were then mixed with acetone in 1:4 weight ratios for 30 minutes. The mixture was allowed to settle for 30 minutes. The liquid layer was then decanted. The solids were dried in a vacuum oven at 80° C. for two hours and then grinded with a coffee grinder to obtain a white powder.

TABLE XV

| INGREDIENTS | WEIGHT (grams) |
|---|---|
| Mixture 1 | |
| Acrylic acid | 2.8 |
| Phosphoric acid mono-ester of polypropylene glycol mono-methacrylate (MW = 500) | 108.0 |
| Phosphoric acid di-ester of polypropylene glycol mono-methacrylate (MW = 900) | 11.0 |
| Polyproplyeneglycol mono-methacrylate (MW = 400) | 5.0 |
| Tergital TMN-6* | 5.0 |
| Water | 338.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals.

Example 16

Use of Network Polymer Compositions XV in a Moisturizer, Composition

The moisturizing formulations of Example 16 were made by combining the listed ingredients in the relative amounts set forth in Table XVI, according to the following procedures. Network Polymer Composition XV were prepared according to Example 15. The ingredients were mixed using Speed mixer at 3000 RPM for 2 minutes. Panel tests showed that Sample 16, when applied on skin, provided lower after-rub-in tack and more cushioning feel than Comparative Sample 16-1. Comparative sample 16-2 was not a stable mixture.

TABLE XVI

| Ingredients | Sample 16 Weight (grams) | Comparative Sample 16A Weight (grams) | Comparative Sample 16B Weight (grams) |
|---|---|---|---|
| Network polymer composition XV | 0.5 | 0.5 | 0 |
| Glycerin | 1 | 1 | 1 |
| D.I. water | 7 | 8.5 | 7.5 |
| *Velvesil 125 | 1.5 | 0 | 1 |

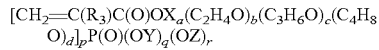
*Velvesil 125 is a silicone gel product, available at Momentive Performance Materials.

Results:
Result Summary:
Examples 1-5, 15 presented six synthesis examples, each representing a different structure. Examples 6-10 showed how these polymer network compositions thickened water at different solids levels or pH. Example 11 proved that the polymer network composition of the present invention could significantly improve the sensory of a moisturizer formulation, compared with Hispagel 2000, a benchmark product. In Example 12, the polymer network composition showed to provide a lighter, silkier sensory in a sunscreen formulation, as well as oil-in-water emulsifying capability. Example 13 showed that the polymer could help to disperse hydrophilic pigment in a color cosmetic formulation. Example 14 showed that this polymer network composition could bring the softness and sleekness feels to hair when incorporated in a rinse-off hair conditioner formulation. Example 16 showed a synergistic effect between the present structure and a silicone gel.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

What is claimed is:
1. A network polymer composition comprising the reaction product of:
   i) at least one anionic polymerizable ethylenically unsaturated monomer (I) selected from the group consisting of

[CH$_2$=C(R$_3$)C(O)OX$_a$(C$_2$H$_4$O)$_b$(C$_3$H$_6$O)$_c$(C$_4$H$_8$O)$_d$]$_p$P(O)(OY)$_q$(OZ)$_r$ where
   R$_3$=H or alkyl of 1 to about 6 carbon atoms;
   X=alkyl, aryl, or alkaryl diradical connecting group of 1 to about 9 carbon atoms; a is 1 to about 100;
   b is 0 to about 100;

c is 0 to about 100;
   d is 0 to about 100;
   q is 0 to about 2;
   r is 0 to about 2;
   p is 1 to about 3 subject to the limitation that p+q+r=3; and
   Y and Z is H, or metal ion;
   wherein at least one of b, c and d is at least 1; and CH$_2$=C(R$_3$)C(O)OX$_{a'}$(C$_2$H$_4$O)$_{b'}$(C$_3$H$_6$O)$_{c'}$(C$_4$H$_8$O)$_{d'}$—SO$_3$—Y

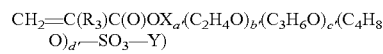

where
   R$_3$=H or alkyl of from 1 to about 6 carbon atoms;
   X=alkyl, aryl, or alkaryl diradical connecting group of 1 to about 9 carbon atoms;
   a' is 1 to about 100;
   b' is 0 to about 100;
   c' is 0 to about 100;
   d' is 0 to about 100;
   Y is H, or metal ion; and
   wherein at least one of b', c' and d' is at least 1;
   (ii) one or more additional monomers (II) selected from the group consisting of acrylic acid/acrylate, methacrylic acid/methacrylate, acrylamides, vinyl acetate and styrene, which are copolymerizable with (I);
   (iii) a cross-linking agent (III), containing at least one ethylenically unsaturated group and capable of copolymerizing with (I) and (II) wherein the network polymer is simultaneously polymerized and cross-linked; and,
   (iv) a thermally activating initiator or redox initiator.

2. The network composition of claim 1 wherein said cross-linking agent is a polyfunctional vinylidene monomer containing at least two unsaturated groups.

3. The network composition of claim 2 wherein said polyfunctional vinylidene monomer is selected from the group consisting of butadiene, isoprene, divinyl benzene, allyl acrylates, polyalkylene glycol diacrylates, and dimethacrylates, Trimethylolpropane trimethacrylate, diallyl esters, and dimethallyl esters.

4. The network composition of claim 1 wherein at least one of b, c, and d, is from 8 to 50 and at least one of b', c' and d' is from 8 to 50.

5. The network composition of claim 1 wherein d and d' are from 1 to 50.

6. The network composition of claim 1 wherein said composition is swollen by a solvent to form a solid, semi-solid, or creamy consistency composition.

7. The network composition of claim 6 wherein said solvent is water.

8. The network composition of claim 1 wherein said composition comprises about 40 to about 99 weight percent based on the total weight of the monomers of said at least one anionic polymerizable ethylenically unsaturated monomer (I), about 0.5 to about 50 weight percent based on the total weight of the monomers of said additional monomers and about 0.1 to about 10 weight percent based on the total weight of the monomers of said cross-linking agent.

9. The network composition of claim 1 wherein said cross-linking agent (III) is at least one anionic polymerizable ethylenically unsaturated monomer (I) selected from the group consisting of

[CH$_2$=C(R$_3$)C(O)OX$_a$(C$_2$H$_4$O)$_b$(C$_3$H$_6$O)$_c$(C$_4$H$_8$O)$_d$]$_p$P(O)(OY)$_q$(OZ)$_r$

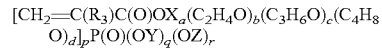

where
R$_3$=H or alkyl of 1 to about 6 carbon atoms;
X=alkyl, aryl, or alkaryl diradical connecting group of 0 to about 9 carbon atoms; a is 0 to about 100;

b is 0 to about 100;
c is 0 to about 100;
d is 0 to about 100;
q is 0 or 1;
r is 0 or 1; and
p is 2 to about 3 subject to the limitation that p+q+r=3; Y and Z is H, or metal ion.

10. The network composition of claim 1 wherein said monomer (I) is selected from the group consisting of $CH_2=C(CH_3)C(O)O(C_3H_6O)_6P(O)(OH)(ONa)$, $CH_2=C(CH_3)C(O)O(C_3H_6O)_6P(O)(OH)_2$ and $CH_2=CHC(O)O(C_3H_6O)_6P(O)(OH)_2$;
said additional monomers (II) are selected from the group consisting of: $CH_2=CHC(O)OH$ and $CH_2=C(CH_3)C(O)O(C_3H_6O)_6H$; and
said cross-linking agent (III) is selected from the group consisting of $[CH_2=C(CH_3)CO_2CH_2]_3CC_2H_5$ and $[CH_2=C(CH_3)C(O)O(C_3H_6O)_6]_2P(O)(OH)$.

11. The network composition of claim 1 wherein the thermally activated or redox initiator is a peroxy or azo compound.

12. The network composition of claim 11 wherein the peroxy compound is selected from the group consisting of hydrogen peroxide, ammonium persulfate, potassium persulfate, diisopropyl peroxide, dilauryl peroxide; di-t-butyl peroxide, dicumyl peroxide, t-butyl hydrogen peroxide, t-amyl hydrogen peroxide, cumyl hydrogen peroxide, acetyl peroxide, lauroyl peroxide, benzoyl peroxide, ethyl peroxybenzoate and pavalate peroxide, and the azo compound is selected from the group consisting of 2-azobis(isobutyronitrile) and 1-azobis(1-cyclohexanecarbonitrile).

13. The network composition of claim 1 in combination with one or more of demulsifying agents, agricultural agents, cosmetics, sunscreen agents, hair conditioners, moisturizers, household cleaners, or coating waxes.

14. The product composition of claim 1 wherein at least one of Y and Z is a metal ion.

15. The product composition of claim 1 having an oil and/or water swellability of 5 to 500 times its original volume.

16. A method for producing network polymer compositions comprising the reaction product of:
i) at least one anionic polymerizable ethylenically unsaturated monomer (I) selected from the group consisting of

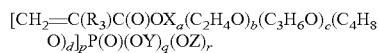

where
$R_3$=H or alkyl of 1 to about 6 carbon atoms;
X=alkyl, aryl, or alkaryl diradical connecting group of 1 to about 9 carbon atoms; a is 1 to about 100;
b is 0 to about 100;
c is 0 to about 100;
d is 0 to about 100;
q is 0 to about 2;
r is 0 to about 2;
p is 1 to about 3 subject to the limitation that p+q+r=3; and
Y and Z is H, or metal ion;
wherein at least one of b, c and d is at least 1; and

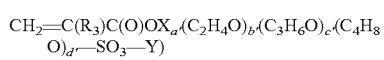

where
$R_3$=H or alkyl of from 1 to about 6 carbon atoms;
X=alkyl, aryl, or alkaryl diradical connecting group of 1 to about 9 carbon atoms;

a' is 1 to about 100;
b' is 0 to about 100;
c' is 0 to about 100;
d' is 0 to about 100;
Y is H, or metal ion; and
wherein at least one of b',c' and d' is at least 1;
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), containing at least one ethylenically unsaturated group and capable of copolymerizing with (I) and (II) wherein the network polymer is simultaneously polymerized and cross-linked; and,
(iv) a thermally activated initiator or redox initiator, the method comprising:
polymerizing monomer (I) and monomer (II) under free radical polymerization conditions in the presence of crosslinking agent (III) to produce a crosslinked network polymer composition and, optionally, subjecting said crosslinked network polymer composition to low or high sheer to adjust viscosity and/or sensory feel of said network composition.

17. The method for producing said network composition of claim 16 wherein said cross-linking agent is a polyfunctional vinlylidene monomer containing at least two unsaturated groups.

18. The method for producing said network composition of claim 17 said polyfunctional monomer is selected from the group consisting of butadiene, isoprene, divinyl benzene, allyl acrylates, polyalkylene glycol diacrylates and dimethacrylates, diallyl esters, and dimethallyl esters.

19. The method for producing said network composition of claim 16 wherein said composition comprises about 40 to about 99 weight percent based on the total weight of the monomers of said at least one anionic polymerizable ethylenically unsaturated monomer (I), about 0.5 to about 50 weight percent based on the total weight of the monomers of said additional monomers and about 0.1 to about 10 weight percent based on the total weight of the monomers of said cross-linking agent.

20. The method for producing said network composition of claim 16 wherein at least one of b, c, and d, is from 8 to 50 and at least one of b', c' and d' is from 8 to 50.

21. The method for producing said network composition of claim 16 wherein d and d' are from 1 to 50.

22. The method for producing said network composition of claim 16 wherein said composition is swollen by a solvent.

23. The method for producing said method for producing network polymer compositions of claim 16 wherein said cross-linking agent (III) added to said network composition is at least one anionic polymerizable ethylenically unsaturated monomer (I) selected from the group consisting of

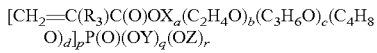

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 or 1;
r is 0 or 1; and
p is 2 to about 3 subject to the limitation that p+q+r=3; Y and Z is H, or metal ion.

24. The method for producing said method for producing network polymer compositions of claim 16 wherein said monomer (I) is selected from the group consisting of $CH_2$=$C(CH_3)C(O)O(C_3H_6O)_6P(O)(OH)(ONa)$, $CH_2$=$C(CH_3)C(O)O(C_3H_6O)_6P(O)(OH)_2$ and $CH_2$=$CHC(O)O(C_3H_6O)_6P(O)(OH)_2$;

said additional monomers (II) are selected from the group consisting of: $CH_2$=$CHC(O)OH$ and $CH_2$=$C(CH_3)C(O)O(C_3H_6O)_6H$; and said cross-linking agent (III) is selected from the group consisting of $[CH_2$=$C(CH_3)_{CO2}CH_2]_3CC_2H_5$ and $[CH_2$=$C(CH_3)C(O)O(C_3H_6O)_6]_2P(O)(OH)$.

25. The method of claim 16 wherein the thermally activated or redox initiator is a peroxy or azo compound.

26. The method of claim 25 wherein the peroxy compound is selected from the group consisting of hydrogen peroxide, ammonium persulfate, potassium persulfate, diisopropyl peroxide, dilauryl peroxide, di-t-butyl peroxide, dicumyl peroxide, t-butyl hydrogen peroxide, t-amyl hydrogen peroxide, cumyl hydrogen peroxide, acetyl peroxide, lauroyl peroxide, benzoyl peroxide, ethyl peroxybenzoate and pavalate peroxide, and the azo compound is selected from the group consisting of 2-azobis(isobutyronitrile) and 1-azobis(1-cyclohexanecarbonitrile).

27. The product composition of claim 16 wherein at least one of Y and Z is a metal ion.

* * * * *